United States Patent
Kaforey et al.

(10) Patent No.: US 6,447,149 B1
(45) Date of Patent: Sep. 10, 2002

(54) SURGICAL LIGHT HANDLE COVER

(75) Inventors: Craig Kaforey, Oakmont, PA (US); Mark Kaforey, Murrysville, PA (US)

(73) Assignee: Xodus Medical, Inc., Murrysville, PA (US)

( * ) Notice: Subject to any disclaimer, the term of this patent is extended or adjusted under 35 U.S.C. 154(b) by 0 days.

(21) Appl. No.: 09/834,117

(22) Filed: Apr. 12, 2001

(51) Int. Cl.⁷ ................................................ F21L 15/12
(52) U.S. Cl. ...................... 362/400; 362/399; 362/804; 16/421; 16/422; 16/436
(58) Field of Search ................................ 362/804, 400, 362/406, 399; 206/223, 438, 439; 16/421, 422, 436, DIG. 12

(56) References Cited

U.S. PATENT DOCUMENTS

| | | |
|---|---|---|
| 4,559,671 A | 12/1985 | Andrews et al. |
| 4,976,299 A | 12/1990 | Bickelman |
| 5,065,296 A | 11/1991 | Cude |
| 5,156,456 A | 10/1992 | Hoftman et al. |
| 5,469,600 A * | 11/1995 | Sandel ..................... 16/421 |
| 5,669,102 A * | 9/1997 | Sandel ..................... 16/421 |
| 5,709,465 A | 1/1998 | Lanzone |
| 5,735,598 A | 4/1998 | Ramirez |
| 5,772,316 A | 6/1998 | Hoftman et al. |
| 5,884,996 A * | 3/1999 | Cottone et al. ............ 16/436 |

* cited by examiner

Primary Examiner—Sandra O'Shea
Assistant Examiner—John Anthony Ward
(74) Attorney, Agent, or Firm—Thorp Reed & Armstrong LLP

(57) ABSTRACT

The present invention provides such a surgical light handle cover with ridges. A second ridge engages the outer rim of the light handle's flange, while a first ridge and a generally conical portion create a suctional force to more securely attach the cover to the non-sterile handle. The ridges and a guard portion help to minimize the chance of accidental contamination. The surgical light handle cover of the present invention is disposable, sterilizable and obviates the need for adhesives to attach the cover to the light handle.

8 Claims, 3 Drawing Sheets

SURGICAL LIGHT HANDLE COVER

FIELD OF THE INVENTION

This invention relates in general to surgical equipment, and more specifically, to disposable covers for surgical light handles.

BACKGROUND OF THE INVENTION

In an operating room, the patient is typically placed on an operating table under an operating room light which illuminates the surgical area for the surgeon. Special lights are used because of the dual requirements for high-powered lighting and maintenance of a sterile environment. These lights typically comprise a bulb or bulbs located within a housing, which is suspended above the operating area. The light projects and focuses the beams upon the surgical area. During the operation, the angle of incidence may need to be adjusted or the light may need to be moved closer to the area which is being operated upon. Because they know best where the light is needed, many surgeons prefer to adjust the operating room lamp themselves rather than instructing someone else to do so. Therefore, it is likely that the light handle of a surgical lamp will come into contact with the hand of the surgeon.

Because a sterile environment must be maintained, the handle of the light's housing must be sterile, even though it may be subject to contact with the hands of the surgeon or other surgical personnel who adjust it.

Because the cost of medical care is constantly escalating, hospital administrators have been forced to search for ways of reducing their facilities' operating costs. Various devices and methods have been proposed in an effort to reduce these ever-increasing costs.

One area in which cost reductions have been sought is in the sterilization of medical equipment. Sterilization is usually accomplished in an autoclave, which is a steam-pressure device for sterilizing devices and instruments. With the ever-increasing number and design of medical instruments, the problems associated with sterilizing a large number of instruments of various sizes and shapes can present a costly burden to the medical facility. In the operating room, all surfaces that may come in contact with the surgeon must be sterile prior to the operation. The sterilization of all surfaces with which the surgeon may come in contact, including surgical light handles, can become extremely burdensome for a medical facility.

One solution to this problem may be to simply dispose of the contaminated item(s). Unfortunately, it is neither practical nor economical to dispose of large operating room fixtures, such as light fixtures after each operation. Because any item touched by any person within the sterile field of an operating room must be sterilized, there must be some way of maintaining the sterility of such large fixtures or steps must be taken to prevent surgical personnel from contacting non-sterile portions of such fixtures.

As another solution, removable handles for operating room lights, can be provided in the operating room. Those handles may be removed and sterilized before each operation. Although it can eliminate the high cost of disposing of fixtures, this solution requires highly paid personnel to remove, clean and sterilize the equipment, expensive materials to wrap the sterilized handles, and the sterilization process itself can be costly.

As a third solution, sterile disposable handles, which can be discarded at the completion of each operation, may be provided. U.S. Pat. No. 4,844,252 to Barron et al. and U.S. Pat. No. 4,974,288 to Reasner disclose examples of such disposable handles. However, use of replaceable operating room lamp handles will not stop the cost escalation because in addition to their cost, disposable handles are bulky, require storage space which is limited at hospitals, and create more hazardous waste. Disposal of the contaminated handles may also expose some hospital personnel to pathogens and disease.

As a result of the above-listed drawbacks, medical facility administrators tend to favor disposable sterile covers for the various surfaces of the operating room subject to contact by operating room personnel. Disposable sterile covers are generally cost effective, because they may be mass-produced and mass-sterilized by a medical manufacturer. Disposable, pre-sterilized covers have the further advantage of being readily available for emergency operations.

Sterile disposable covers are available in the art for covering a non-sterile operating room light handle. U.S. Pat. No. 4,605,124 to Sandel et al. and U.S. Pat. No. 4,976,299 to Bickelman provide examples of such sterile disposable covers. However, each of these disposable covers has some disadvantages.

The invention of Sandel is a disposable cover having a cylindrical grip and integral flange. The cylindrical grip narrows where it attaches to the integral flange to fit the light handle. The flange may either be flat-shaped or bell-shaped, depending on the shape of the handle. The cover has internal reinforcing ribs in the grip portion. At col. 3, lines 41–45, Sandel states that adhesive can be applied to the interior portions of the flange to firmly attach the cover to the handle. It appears that the adhesive is applied to the invention of Sandel to prevent it from inadvertently sliding off the light handle during surgery.

The disposable cover of Sandel also suffers from several other drawbacks. Because the flange is flexible and is adapted to the shape of the handle, the disposable cover does not have a protective guard to prevent the nurse's or surgeon's hand from sliding past the flange and contacting non-sterile portions of the surgical room light fixture. Further, due to the flexibility of the flange, the scrub nurse's or surgeon's glove may become contaminated while applying the cover to the non-sterile light handle. Finally, because the cover of Sandel is intended to be folded prior to shipment, the cover itself may become contaminated from prior folds as it is being applied over the light handle, if the cover edge contacts the non-sterile light handle and/or flange.

The invention of Bickelman is a sterile disposable cover having a cylindrical hollow member and a guard. The guard is intended to prevent the surgeon's hand from contacting non-sterile portions of a light fixture. The cover also includes a retention member that partially closes the opening of the opened end of the cylindrical hollow member. The retention member may be a circular plastic disk with teeth-like projections that is adhered within an annular recessed portion in the guard. However, the disposable cover of Bickelman suffers from the drawbacks that the guard does not appear to be sufficiently rigid nor is it adapted to the shape of the handle and/or light fixture. Thus, it is possible that the surgeon's hand may slide past the guard and contact non-sterile portions of the light fixture. In addition, the retention disk makes application and removal of the cover difficult. The retention disk can also prevent the application of a second cover over the first one, if necessary because of accidental contamination during the surgical procedure.

Therefore, a need exists in the art for a surgical light handle cover that will provide the benefits of disposability, sterilizability, security of attachment to the handle without the need for adhesive and which will help prevent the surgeon's or nurse's hand from accidentally contaminating the handle.

SUMMARY OF THE INVENTION

The present invention provides such a surgical light handle cover with two circular ridges and a guard, which help to minimize the chances of accidental contamination. The surgical light handle cover of the present invention is disposable, sterilizable and will attach to the surgical light handle in a manner which will obviate the need for adhesives.

The present invention also provides a disposable cover for a surgical light handle, comprising a cylindrical portion closed at a first end and tapering outward from a second end to form a generally conical portion, the generally conical portion having a first circular ridge and a second circular ridge thereon, and a guard portion extending from the second circular ridge, wherein the generally conical portion is sized and shaped to rest on a flange of the surgical light handle, the second circular ridge is sized and shaped to engage the outer rim of the flange, the ridges and the guard portion are sized and shaped to prevent contact with the flange by surgical personnel, and the first ridge and the generally conical portion together are capable of creating a suctional force.

The present invention further provides a disposable cover for a surgical light handle, the disposable cover comprising, a cylindrical portion closed at a first end and tapering outward from a second end to form a generally conical portion, the generally conical portion having a first circular ridge and a second circular ridge thereon, and a guard portion extending from the second circular ridge, wherein the generally conical portion rests on a flange of the surgical light handle, the second circular ridge engages the outer rim of said flange, the ridges and the guard portion are sized and shaped to prevent contact with the flange by surgical personnel, and the first ridge and the generally conical portion together are capable of creating a suctional force.

The present invention still further provides a disposable cover for a surgical light handle, the disposable cover comprising, a cylindrical portion closed at a first end and tapering outward from a second end to form a generally conical portion, the generally conical portion having a first circular ridge and a second circular ridge thereon, and a guard portion extending from the second circular ridge, wherein the generally conical portion rests on a flange of the surgical light handle, the second circular ridge engages the outer rim of the flange, the ridges and the guard portion are sized and shaped to prevent contact with the flange by surgical personnel, and the first ridge and said generally conical portion together create a suctional force.

The present invention also further provides a disposable cover for a surgical light handle, the disposable cover comprising, a cylindrical portion having a first end and a second end, the first end being closed; and a generally conical portion connected to and extending from the second end of the cylindrical portion, the conical portion having first and second circular ridges configured to form a suction when the cover is attached to a surgical light handle.

The present invention yet still further provides a method of attaching a surgical light handle cover comprising a cylindrical portion closed at a first end and tapering outward from a second end to form a generally conical portion, the generally conical portion having a first circular ridge and a second circular ridge thereon, and a guard portion extending outwardly from the second circular ridge, wherein the generally conical portion is sized and shaped to rest on a flange of said surgical light handle, the second circular ridge is sized and shaped to engage the outer rim of the flange, the ridges and the guard portion are sized and shaped to prevent contact with the flange by surgical personnel, and the first ridge and the generally conical portion together are capable of creating a suctional force, to a surgical light handle, the method comprising, placing and advancing the surgical light handle cover onto the surgical light handle such that the second ridge engages the outer rim of the flange of the surgical light handle, advancing the surgical light handle cover to a point where the first ridge and the generally cylindrical portion expand with trapped air and further advancing the surgical light handle cover to a point where the first circular ridge and the cylindrical portion force air out of the cover to create a suction.

These and other advantages and benefits of the present invention will be apparent from the Detailed Description of the Invention herein below.

BRIEF DESCRIPTION OF THE FIGURES

The present invention will now be described for the purpose of illustration and not limitation in conjunction with the following figures wherein.

DETAILED DESCRIPTION OF THE INVENTION

Figure 1:
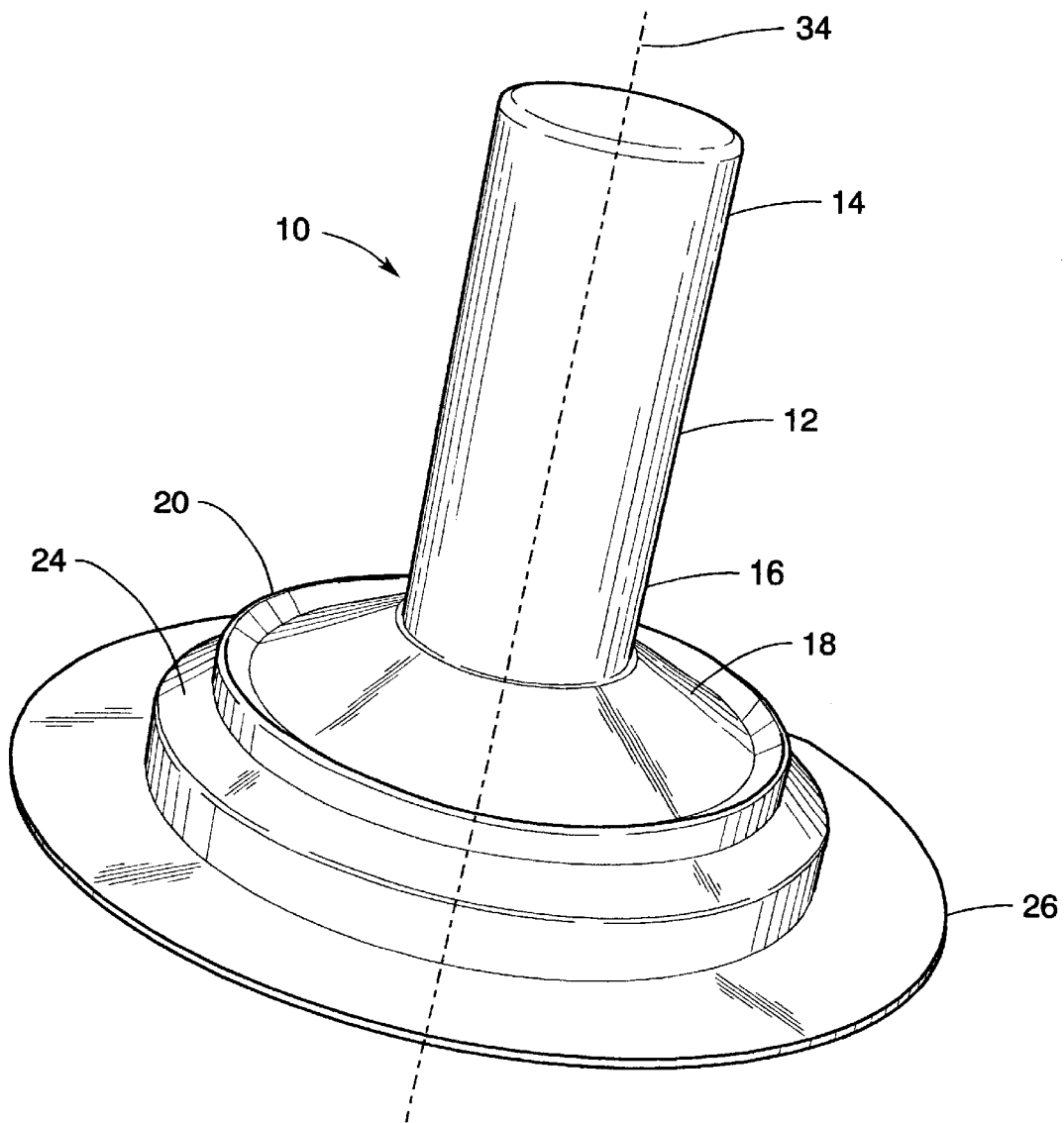
FIG. 1 is a perspective view of the disposable cover of the present invention.

As depicted in FIG. 1, the surgical light handle cover of the present invention 10, comprises a cylindrical portion 12 closed at a first end 14 and tapering outward from an open second end 16 to form a generally conical portion 18. The generally conical portion 18 has a first circular ridge 20 and a second circular ridge 24 thereon, with a circular guard portion 26 extending from the second circular ridge. The cylindrical portion 12, conical portion 18, first ridge 20, second ridge 24 and guard portion 26 are preferably symmetrical about a center axis 34.

The generally conical portion 18 is sized and shaped to preferably lie flat against the flange of a non-sterile surgical light handle. The second circular ridge 24 is sized and shaped to fit snugly around the outer rim of the flange. The circular ridges 20 and 24 and guard portion 26 are also sized and shaped to prevent operating room personnel from contacting the non-sterile light handle when adjusting it. Although the engagement of second circular ridge 24 with the outer rim of the flange of a light handle is sufficient to attach the cover of the present invention to a non-sterile light handle, the first circular ridge 20 and the generally conical portion 18 together can create a suctional force to more securely attach the disposable cover 10 to the surgical light handle as discussed more fully herein below.

The surgical light handle cover of the present invention may preferably be made of a flexible plastic. Preferred by the inventors are flexible, sterilizable plastics including, but not limited to, low density polyethylene, high density polyethylene, polypropylene, polystyrene, polycarbonate, polytetrafluoroethylene, tetrafluoroethylene and fluorinated ethylene propylene and combinations thereof. After being manufactured, the light handle cover of the present invention may preferably be packaged and sterilized in the package by a bulk sterilization process.

Figure 2:
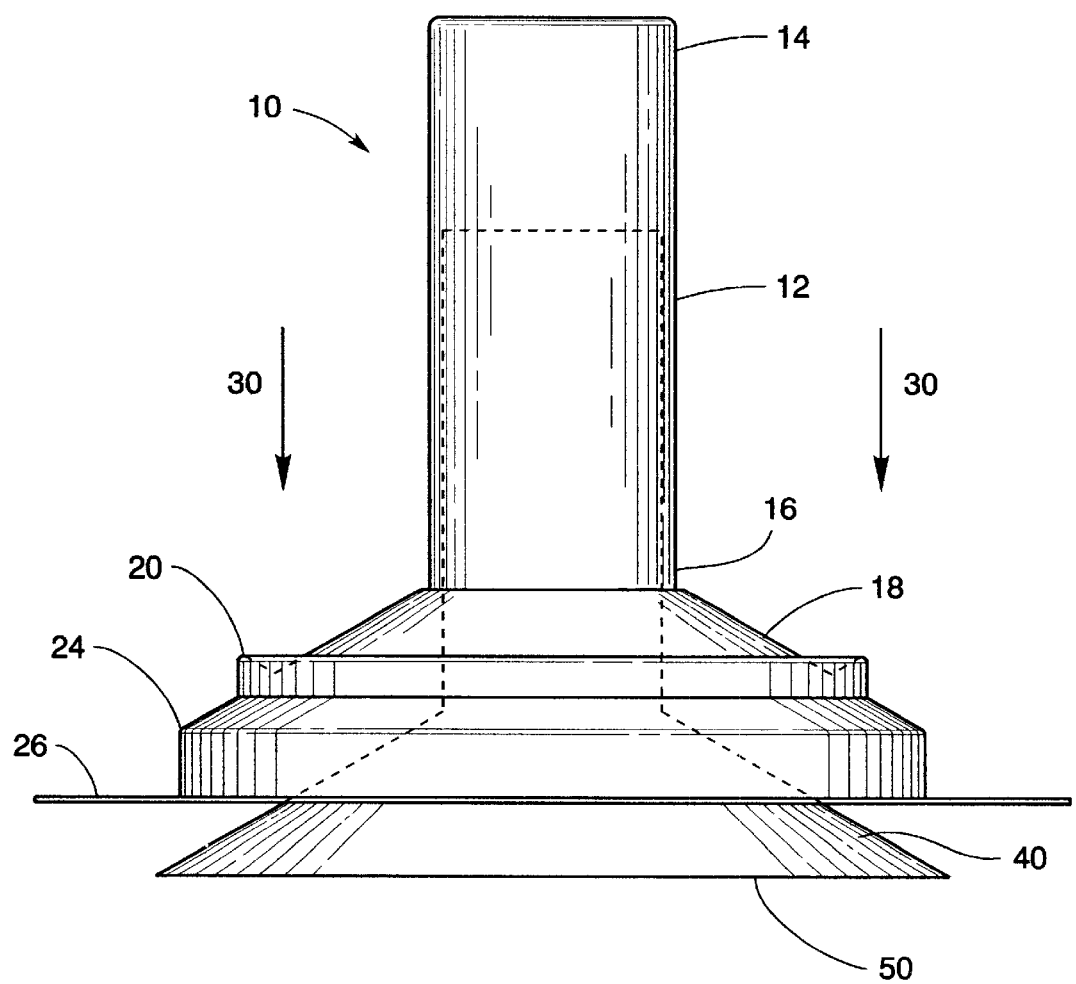
FIG. 2 is a side view of the surgical light handle cover of the present invention showing it being placed upon a surgical light handle.

To use the sterile, disposable cover 10 of the present invention, the package is preferably opened by a non-sterile nurse and the contents transferred into the sterile surgical theater. A scrub nurse picks up the handle cover and places it over a non-sterile surgical light handle 40 as shown in FIG. 2. Alternatively, if the surgical light handle cover 10 has not been pre-sterilized, it must be sterilized prior to its application onto a non-sterile surgical light handle.

Figure 3A:
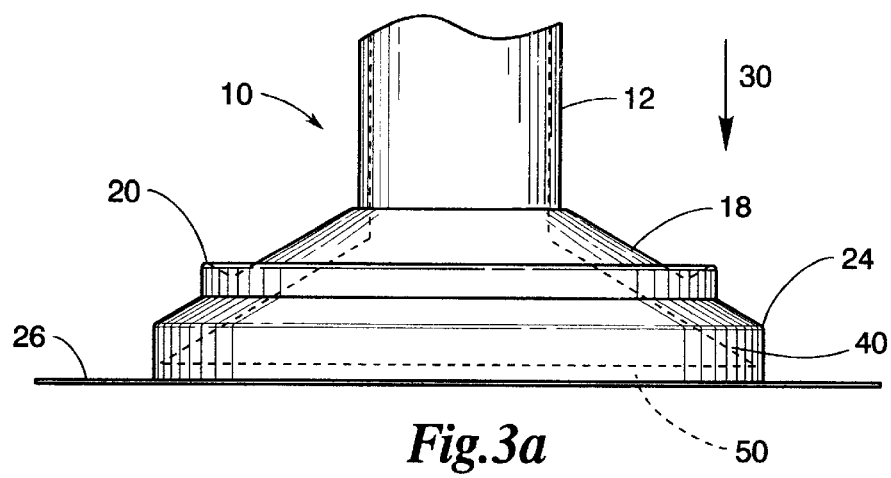
FIGS. 3a, 3b and 3c depict the advancement of the surgical light handle cover of the present invention onto a surgical light handle.

In either case, the cover 10 may be applied to a non-sterile surgical light handle 40 and advanced in the direction of the arrows 30 to a position where the second circular ridge 24 fits tightly around the outer rim 50 of the light handle's flange 40 as shown in FIG. 3a. The inventors prefer that this advancement be accompanied by a twisting motion on the cylindrical portion 12 of the surgical light handle cover. Before the second circular ridge 24 engages the outer rim 50 of the flange 40, the advancement forces air out of the light cover. If an attempt is made to remove the cover after the second circular ridge 20 engages the outer rim 50 of the light handle flange 40, a suction will develop because the engagement makes it difficult for air to re-enter the cover 10. This suction will prevent the surgical light handle cover of the present invention from sliding off the light handle. However, the inventors prefer that the surgical light handle cover of the present invention be fully advanced onto the handle to provide the maximum suctional force.

Figure 3B:
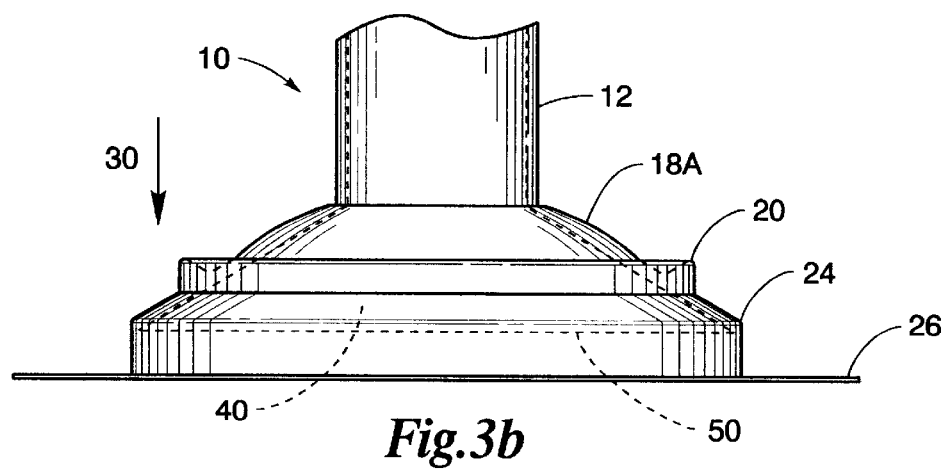
Figure 3C:
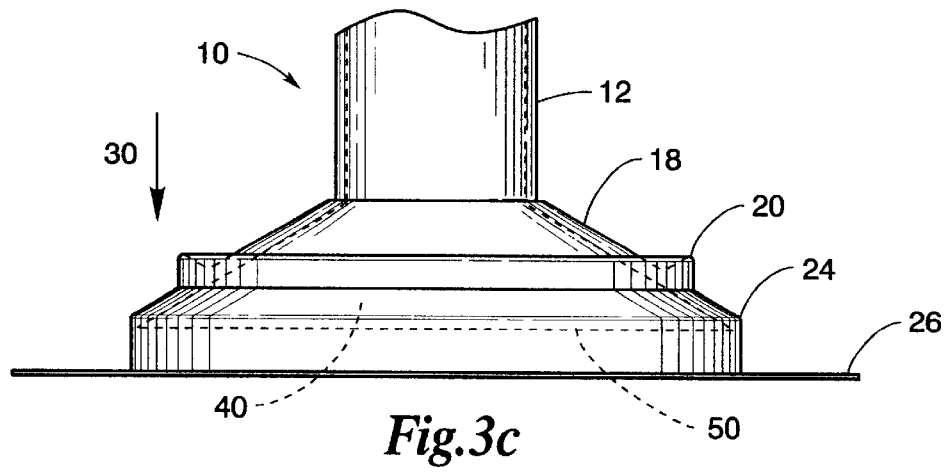

The surgical light handle cover 10 of the present invention can be further advanced to a position as depicted in FIG. 3b. Because the second ridge 24 has engaged the outer rim 50 of the flange 40 thereby restricting outflow, the first circular ridge 20 fills with trapped air and, depending upon the volume of trapped air, facilitates the expansion of a portion 18A of the generally conical portion 18. Further advancement in the direction indicated by the arrow 30 in FIG. 3b causes the portion 18A and the first circular ridge 20 to force out this trapped air. As the first circular ridge 20 and portion 18A return to their original shapes as depicted in FIG. 3c, that will create a suctional force that will keep the sterile surgical light handle cover 10 of the present invention more securely attached to the non-sterile surgical light handle 40 during surgery. After surgery is complete, cleanup personnel can pull off the surgical light handle cover of the present invention and dispose of it along with the other-disposable covers from the operating theater.

The ridges 20 and 24 and guard portion 26 also help keep the hand of the person applying the light handle cover, or adjusting the surgical light, from contacting the non-sterile light handle or flange. Unlike the invention of Bickelman, the surgical light handle cover of the present invention permits the application of a second cover over the first one, if necessary because of accidental contamination during the surgical procedure.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

We claim:

1. A disposable cover for a surgical light handle, said disposable cover comprising:

a cylindrical portion closed at a first end and tapering outward from a second end to form a generally conical portion, said generally conical portion having a first circular ridge and a second circular ridge thereon, and a guard portion extending from said second circular ridge, wherein said generally conical portion is sized and shaped to rest on a flange of said surgical light handle, said second circular ridge is sized and shaped to engage the outer rim of said flange, said ridges and said guard portion are sized and shaped to prevent contact with said flange by surgical personnel, and said first ridge and said generally conical portion together are capable of creating a suctional force.

2. The disposable cover of claim 1, wherein said cover comprises flexible plastic.

3. The disposable cover of claim 2, wherein said flexible plastic is sterilizable.

4. The disposable cover of claim 3, wherein said sterilizable flexible plastic is a member selected from the group consisting of low density polyethylene, high density polyethylene, polypropylene, polystyrene, polycarbonate, polytetrafluoroethylene, tetrafluoroethylene and fluorinated ethylene propylene and combinations thereof.

5. A disposable cover for a surgical light handle, said disposable cover comprising:

a cylindrical portion closed at a first end and tapering outward from a second end to form a generally conical portion, said generally conical portion having a first circular ridge and a second circular ridge thereon, and a guard portion extending from said second circular ridge, wherein said generally conical portion rests on a flange of said surgical light handle, said second circular ridge engages the outer rim of said flange, said ridges and said guard portion are sized and shaped to prevent contact with said flange by surgical personnel, and said first ridge and said generally conical portion together are capable of creating a suctional force.

6. A disposable cover for a surgical light handle, said disposable cover comprising:

a cylindrical portion closed at a first end and tapering outward from a second end to form a generally conical portion, said generally conical portion having a first circular ridge and a second circular ridge thereon, and a guard portion extending from said second circular ridge, wherein said generally conical portion rests on a flange of said surgical light handle, said second circular ridge engages the outer rim of said flange, said ridges and said guard portion are sized and shaped to prevent contact with said flange by surgical personnel, and said first ridge and said generally conical portion together create a suctional force.

7. A disposable cover for a surgical light handle, comprising:

a cylindrical portion having a first end and a second end, said first end being closed; and a generally conical portion connected to and extending from said second end of said cylindrical portion, said conical portion having first and second circular ridges configured to form a suction when said cover is attached to a surgical light handle.

8. A method of attaching a surgical light handle cover comprising a cylindrical portion closed at a first end and tapering outward from a second end to form a generally conical portion, said generally conical portion having a first circular ridge and a second circular ridge thereon, and a guard portion extending outwardly from said second circular ridge, wherein said generally conical portion is sized and shaped to rest on a flange of said surgical light handle, said second circular ridge is sized and shaped to engage the outer rim of said flange, said ridges and said guard portion are sized and shaped to prevent contact with said flange by surgical personnel, and said first ridge and said generally conical portion together are capable of creating a suctional force, to a surgical light handle, said method comprising:

placing and advancing said surgical light handle cover onto said surgical light handle such that said second ridge engages said outer rim of said flange of said surgical light handle;

advancing said surgical light handle cover to a point where said first ridge and said generally cylindrical portion expand with trapped air; and further advancing said surgical light handle cover to a point where said first circular ridge and said cylindrical portion force air out of said cover to create a suction.

\* \* \* \* \*